United States Patent
Ezaki et al.

(10) Patent No.: US 11,458,223 B2
(45) Date of Patent: Oct. 4, 2022

(54) DISCHARGE DEVICE AND ELECTRIC MACHINE

(71) Applicant: SHARP KABUSHIKI KAISHA, Sakai (JP)

(72) Inventors: Tetsuya Ezaki, Sakai (JP); Nobuyuki Ohe, Sakai (JP); Takahiro Matsuyama, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 469 days.

(21) Appl. No.: 16/609,572

(22) PCT Filed: Sep. 1, 2017

(86) PCT No.: PCT/JP2017/031552
§ 371 (c)(1),
(2) Date: Oct. 30, 2019

(87) PCT Pub. No.: WO2018/207385
PCT Pub. Date: Nov. 15, 2018

(65) Prior Publication Data
US 2020/0054780 A1    Feb. 20, 2020

(30) Foreign Application Priority Data
May 9, 2017  (JP) .............................. JP2017-093042

(51) Int. Cl.
*H01T 23/00*    (2006.01)
*A61L 9/22*    (2006.01)
(Continued)

(52) U.S. Cl.
CPC ................. *A61L 9/22* (2013.01); *A61L 9/046* (2013.01); *A61L 9/122* (2013.01); *H01T 23/00* (2013.01);
(Continued)

(58) Field of Classification Search
None
See application file for complete search history.

(56) References Cited

U.S. PATENT DOCUMENTS

2011/0114192 A1* 5/2011 Kim ..................... B41J 2/095
                                                                137/13
2012/0256555 A1* 10/2012 Nakajima .......... H05B 41/2928
                                                                315/224

(Continued)

FOREIGN PATENT DOCUMENTS

CN        101752796 A    6/2010
CN        105493361 A    4/2016
(Continued)

*Primary Examiner* — Stephen W Jackson
(74) *Attorney, Agent, or Firm* — ScienBiziP, P.C.

(57) ABSTRACT

Provided is a discharge device that can improve the efficiency of generating reactive species. The discharge device includes a discharging unit, which has a tip end and discharges from the tip end in response to an application of a voltage, an induction electrode, which forms an electric field between the induction electrode end the discharging unit, and a second electrode, which is disposed between the discharging unit and the induction electrode and receives a voltage having a polarity the same as a polarity of the voltage applied to the discharging unit.

9 Claims, 8 Drawing Sheets

(51) Int. Cl.
*A61L 9/04* (2006.01)
*A61L 9/12* (2006.01)

(52) U.S. Cl.
CPC ..... *A61L 2209/16* (2013.01); *A61L 2209/212* (2013.01)

(56) References Cited

U.S. PATENT DOCUMENTS

| | | |
|---|---|---|
| 2016/0111859 A1 | 4/2016 | Katano |
| 2016/0204581 A1 | 7/2016 | Nishida et al. |

FOREIGN PATENT DOCUMENTS

| | | |
|---|---|---|
| CN | 105990791 A | 10/2016 |
| JP | 2008-034220 A | 2/2008 |
| JP | 2011-054308 A | 3/2011 |
| JP | 5461736 B1 | 4/2014 |
| JP | 2014-120225 A | 6/2014 |

* cited by examiner

DISCHARGE DEVICE AND ELECTRIC MACHINE

TECHNICAL FIELD

The present disclosure relates to a discharge device and an electric machine. The present disclosure claims priority to Japanese Patent Application No. 2017-093042 filed in the Japan Patent Office on May 9, 2017. The entire contents of which are incorporated herein by reference.

BACKGROUND ART

Disclosed thus far is a discharge device including a bundled electrode having a structure in which multiple thin wires are bundled into a brush shape, and the bundled multiple thin wires are disposed on a substrate covered with an insulator (refer to, for example, Japanese Unexamined Patent Application Publication No. 2008-34220 (PLT 1)).

CITATION LIST

Patent Literature

PTL 1: Japanese Unexamined Patent Application Publication No. 2008-34220

SUMMARY OF INVENTION

Technical Problem

In the discharge device described in the above literature, the insulator that holds the bundled electrode is disposed closer to the bundled electrode than counter electrodes. When a high voltage is applied to the bundled electrode, reactive species are generated. Here, the insulator located adjacent to the bundled electrode may collect the generated reactive species, and prevent the reactive species from being efficiently discharged to the space. If the thin wires come into contact with the insulator during use of the discharge device for a long term, the performance of the discharge device is significantly degraded.

The present disclosure provides a discharge device that can improve the efficiency of generating reactive species.

Solution to Problem

The present disclosure provides a discharge device that includes a discharging unit, an induction electrode, and a second electrode. The discharging unit has a tip end, from which the discharging unit discharges in response to an application of a voltage. The induction electrode forms an electric field between itself and the discharging unit. The second electrode is disposed between the discharging unit and the induction electrode, and receives a voltage having a polarity the same as the polarity of the voltage applied to the discharging unit.

In the above discharge device, the second electrode is spaced apart from the tip end by a distance smaller than a shortest distance between the tip end and the induction electrode.

The above discharge device also includes resin with which the induction electrode and the second electrode are sealed.

The above discharge device also includes a substrate. The substrate has a surface. The substrate supports the discharging unit. The second electrode is disposed at a root portion of the discharging unit that protrudes from the surface of the substrate.

In the above discharge device, the second electrode is disposed on the surface of the substrate.

In the above discharge device, the induction electrode is disposed on the surface of the substrate. The surface of the substrate has a slit recessed between the second electrode and the induction electrode.

In the above discharge device, the discharging unit includes multiple linear electric conductors and a base portion that bundles the electric conductors.

In the above discharge device, the second electrode has a disk shape having substantially the same diameter as that of a projection of a movable range of the electric conductor on the surface of the substrate.

An electric machine according to the present disclosure includes the discharge device according to any one of the above aspects, and a blower that feeds gas to the discharge device.

Advantageous Effects of Invention

The discharge device according to the present disclosure can improve the efficiency of generating reactive species.

DESCRIPTION OF EMBODIMENTS

Embodiments will be described below with reference to the drawings. The same or equivalent components are denoted with the same reference signs, and may not be described repeatedly.

First Embodiment

[Air Cleaner 100]

Figure 1:
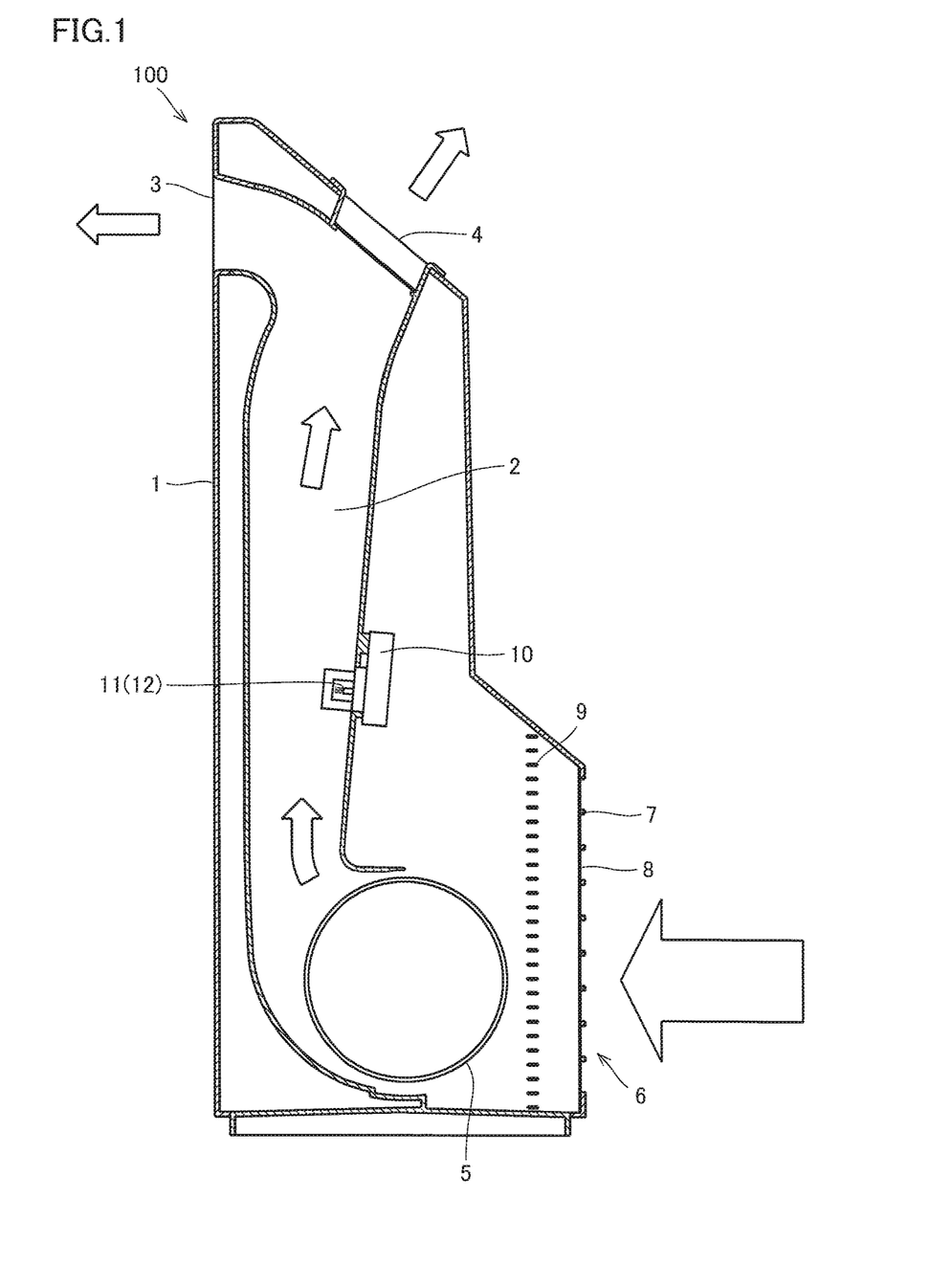
FIG. 1 is a schematic cross-sectional view of a structure of an air cleaner including a discharge device according to an embodiment.

FIG. 1 is a cross-sectional view of a schematic structure of an air cleaner 100 including a discharge device 10 according to an embodiment. The air cleaner 100 includes an outer casing 1, which forms the exterior of the air cleaner 100. The left side in FIG. 1 corresponds to the front side of the air cleaner 100 or the front side of the outer casing 1. The right side in FIG. 1 corresponds to the rear side of the air cleaner 100 or the rear side of the outer casing 1.

A duct 2 vertically extends inside the outer casing 1. Hollow arrows in FIG. 1 denote the directions in which gas, typically, air flows in the duct 2. A first outlet 3 and a second outlet 4 are formed at an upper portion of the outer casing 1. The first outlet 3 is formed in the front surface at the upper portion of the outer casing 1. The second outlet 4 is formed in the rear surface at the upper portion of the outer casing 1. The first outlet 3 and the second outlet 4 are disposed at the upper end of the duct 2. The first outlet 3 and the second outlet 4 are disposed at the downstream end in the direction in which air flows in the duct 2. The duct 2 is open to the outside of the outer casing 1 at the first outlet 3 and the second outlet 4.

A blower 5 is disposed in an upstream end opening of the duct 2. The blower 5 is disposed at a lower portion of the outer casing 1. The blower 5 is disposed in a lower end opening of the duct 2. The blower 5 delivers gas sucked through an inlet port 6 into the duct 2. The blower 5 is, for example, a cross flow fan, but not particularly limited to this.

The inlet port 6 is formed in the rear surface at a lower portion of the outer casing 1. A resin-made gridlike grille 7 is disposed at the inlet port 6. A thin mesh filter 8 is attached to the inner side of the grille 7. A fan guard 9 is disposed behind the filter 8 (on the inner side of the outer casing 1). The fan guard 9 is disposed between the inlet port 6 and the blower 5. The fan guard 9 is disposed to prevent foreign matter from entering the blower 5. The upstream end of the duct 2 in the direction in which air flows in the duct 2 is disposed to face the inlet port 6 with the fan guard 9 interposed therebetween.

The discharge device 10 is disposed at a center portion of the duct 2 in the vertical direction. The discharge device 10 is disposed between the upper end and the lower end of the duct 2. The discharge device 10 is attached to the wall surface of the duct 2 on the rear surface. The discharge device 10 may be disposed at any portion between the upstream end and the downstream end in the direction in which air flows in the duct 2, instead of being attached to the wall surface of the duct 2 on the rear surface, as illustrated in FIG. 1. For example, the discharge device 10 may be attached to the wall surface of the duct 2 on the front surface, or the wall surface of the duct 2 on the side surface.

The discharge device 10 includes discharging units 11 and 12, described in detail later, and a housing 20 (refer to FIG. 2 and other drawings). The housing 20 of the discharge device 10 is fixed to the wall surface of the duct 2, and disposed outside of the duct 2. The discharging units 11 and 12 are disposed inside the duct 2. These two discharging units 11 and 12 are arranged side by side in the direction perpendicular to the direction in which air flows in the duct 2 (arranged in the depth direction of FIG. 1).

During the operation of the air cleaner 100, the blower 5 and the discharge device 10 operate while receiving power supply. The discharging units 11 and 12 discharge with an application of a voltage to generate reactive species such as ions, electrons, radicals, and ozone. Ions generated by the discharging units 11 and 12 may contain positive ions only, negative ions only, or both the positive ions and the negative ions.

When the blower 5 operates, gas is sucked into the outer casing 1 through the inlet port 6, and flows into the duct 2. Gas flows upward from the bottom through the duct 2 and passes by the discharge device 10. Reactive species generated by the discharge device 10 flow toward the upper end of the duct 2 together with the gas, and flow out of the duct 2 through the first outlet 3 and the second outlet 4 to be discharged out of the air cleaner 100. The gas and the reactive species are discharged from the first outlet 3 toward the front side of the air cleaner 100. The gas and reactive species are discharged obliquely to the rear of the air cleaner 100 from the second outlet 4.

The discharge device 10 according to the present embodiment can be used in electric machines of various different types other than the air cleaner 100. The discharge device 10 may be included in, for example, an ion generator, an air conditioner (including car-mounted air conditioner), a ventilator, a refrigerator, a washing machine, a cleaner, a dryer, a humidifier, a dehumidification machine, a hair dryer, a ceramic fan heater, or an electric fan.

[Discharge Device 10]

Figure 2:
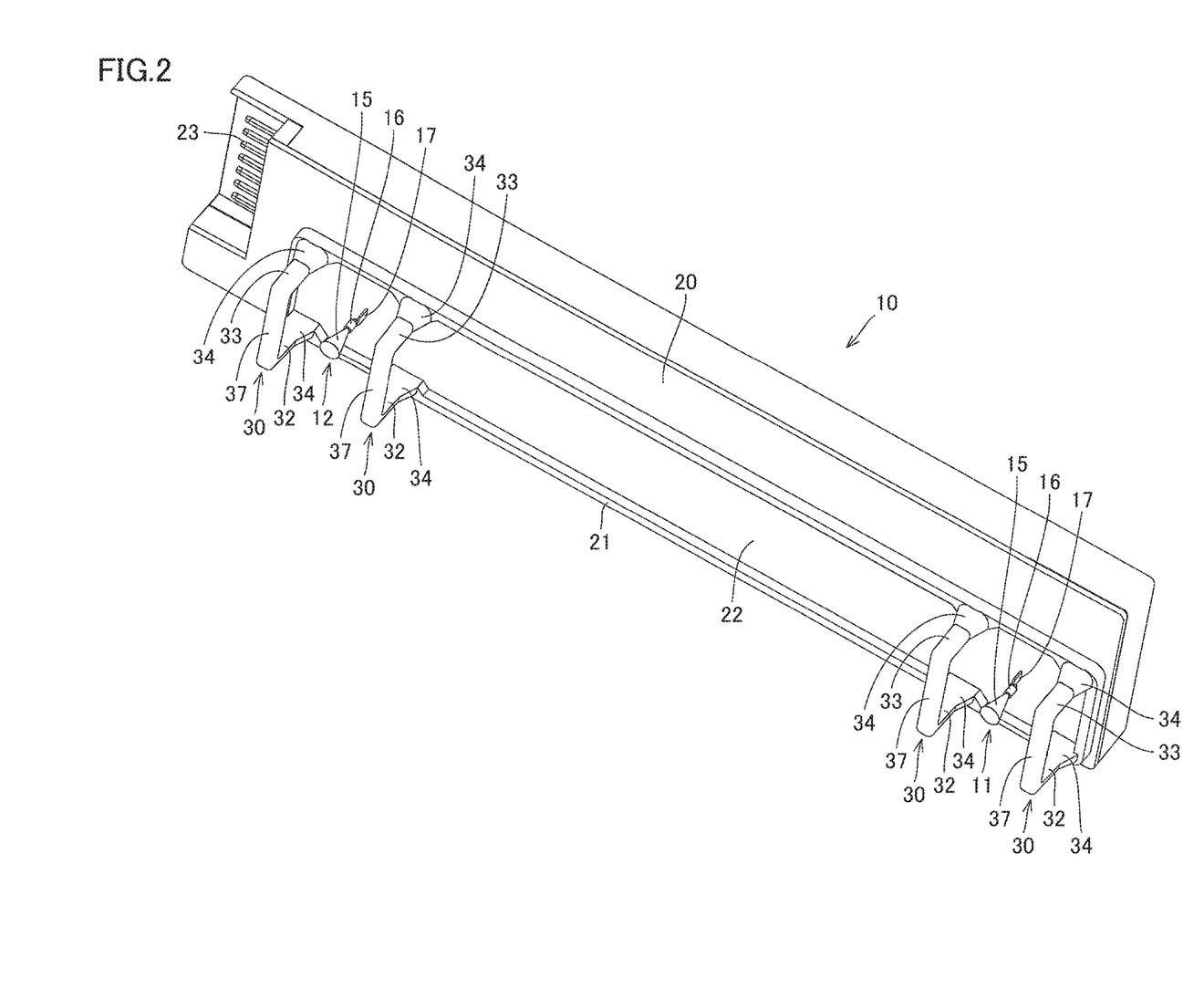
FIG. 2 is a perspective view of a discharge device according to an embodiment.
Figure 3:
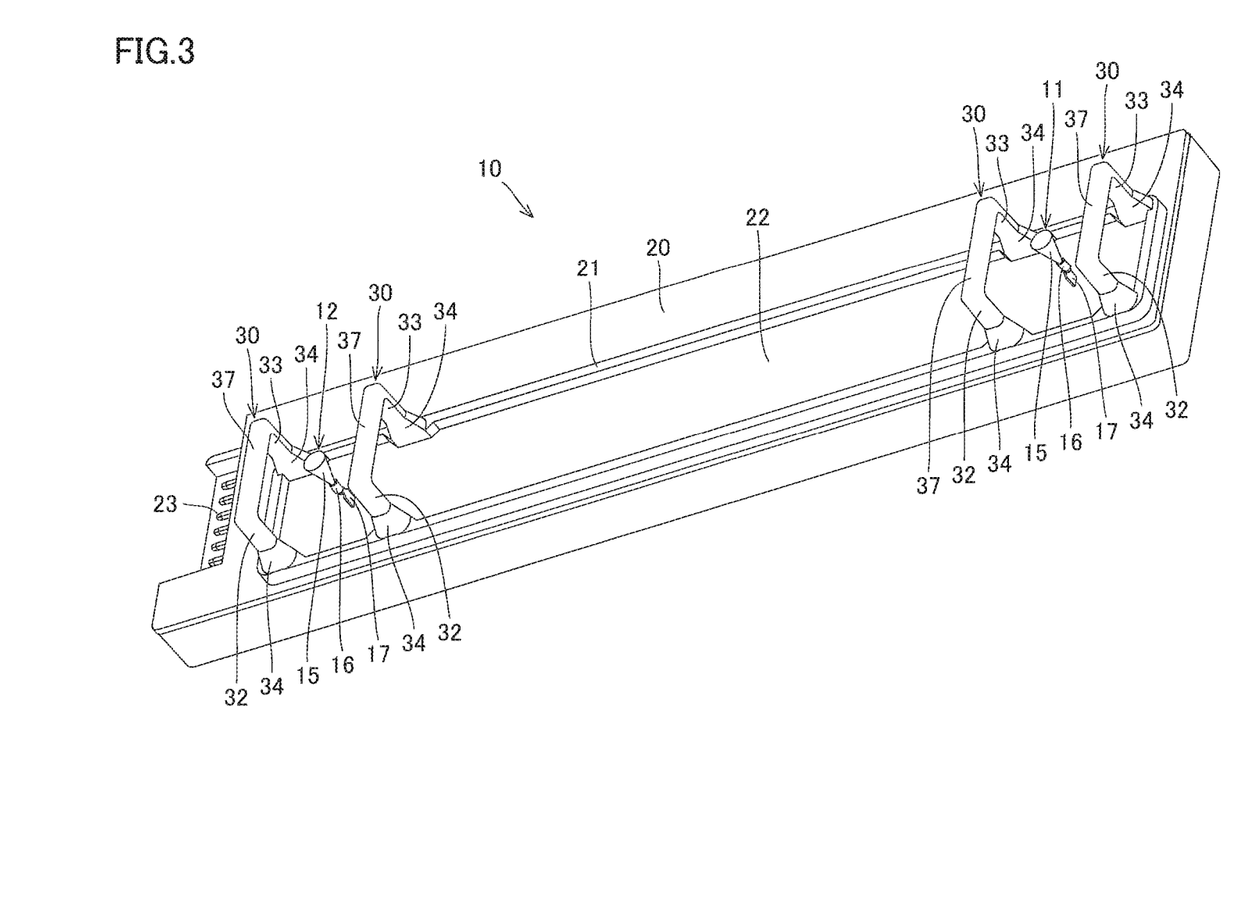
FIG. 3 is a perspective view of the discharge device illustrated in FIG. 2, viewed from a different angle.

FIG. 2 is a perspective view of the discharge device 10 according to an embodiment. FIG. 3 is a perspective view of the discharge device 10 illustrated in FIG. 2, viewed from a different angle.

The discharge device 10 includes the discharging units 11 and 12 and the housing 20. The discharging units 11 and 12 protrude from the housing 20. The discharging units 11 and 12 extend in the direction in which the discharging units 11 and 12 protrude from the housing 20.

The discharging units 11 and 12 include multiple electric conductors 15 with a linear shape. The linear shape includes a thread shape, a fiber shape, and a wire shape. The electric conductors 15 are formed from an electroconductive material. The electric conductors 15 may be made of, for example, metal, carbon fiber, electroconductive fiber, or electroconductive resin. The electric conductors 15 each have a base end portion, located closer to the housing 20, and a far end portion, located away from the housing 20. The far end portions of the multiple electric conductors 15 form a brush shape.

The outer diameter of each of the electric conductors 15 falls within the range of 5 μm to 30 μm. The electric conductors 15 having a thickness of larger than or equal to 5 μm have reliable mechanical strength, and less electric abrasion. The electric conductors 15 having a thickness of smaller than or equal to 30 μm bend like a hair, and easily spread and wave.

The electric conductors 15 may be formed of, for example, carbon fiber with an outer diameter of 7 μm, or electroconductive fiber made of stainless steel with an outer diameter of 12 μm or 25 μm.

The discharging units 11 and 12 each include a base portion 16 that bundles the multiple electric conductors 15. The base portion 16 has a tube shape, typically, a cylindrical tube profile. The base portion 16 is caulked while surrounding the base end portions of the multiple electric conductors 15 to support the multiple electric conductors 15 at their base end portions. The base portion 16 bundles the base end portions of the electric conductors 15.

The electric conductors 15 that protrude from the base portions 16 by a small length may fail to fully bend, and spread and wave insufficiently. To improve the discharging efficiency of the discharging units 11 and 12, the electric conductors 15 protrude from the base portions 16 by a length of larger than or equal to 3 mm. The electric conductors 15 may protrude from the base portions 16 by a length larger than or equal to 4.5 mm.

The discharging units 11 and 12 each include a support portion 17 that supports the corresponding base portion 16. The support portion 17 has a flat plate shape. The support portion 17 of each of the discharging units 11 and 12 is in contact with the tube-shaped base portions 16 at the end portions away from the housing 20 in the longitudinal direction.

The longitudinal direction of the discharging units 11 and 12 is the direction in which the discharging units 11 and 12 protrude from the housing 20. The discharging units 11 and 12 are brush-shaped electrodes whose longitudinal direction is the direction in which they protrude from the housing 20, and each of which include multiple linear electric conductors 15 and the base portion 16 that bundles the electric conductors 15.

The housing 20 is made of an insulating resin. The housing 20 has a profile of a substantially rectangular parallelepiped box. The housing 20 has a substantially rectangular shape in a plan view. The housing 20 has an angular-tube-shaped wall portion 21, which protrudes from the surface of the housing 20. The wall portion 21 has a substantially rectangular frame shape in a plan view. The longitudinal direction of the housing 20 coincides with the longitudinal direction of the wall portion 21. The discharging unit 11 is disposed at a first end portion of the housing 20 in the longitudinal direction. The discharging unit 12 is disposed at a second end portion of the housing 20 in the longitudinal direction.

The space surrounded by the wall portion 21 constitutes a container portion. The container portion is filled with resin 22. Examples of the resin 22 include an insulating material such as epoxy resin or polyurethane resin. The discharging units 11 and 12 are disposed perpendicular to the surface of the resin 22. The discharging units 11 and 12 protrude from the surface of the resin 22. The discharging units 11 and 12 protrude from the housing 20. The housing 20 includes a connector 23 for external connection.

The discharge device 10 includes electrode protectors 30, which protect the tips of the discharging units 11 and 12. Each electrode protector 30 is disposed adjacent to a corresponding one of the discharging units 11 and 12 to prevent an object out of the discharge device 10 from directly coming into contact with the discharging unit 11 or 12. The electrode protectors 30 are integrally formed with the housing 20 to protrude from the surface of the housing 20. The electrode protectors 30 protrude further from the surface of the housing 20 than the discharging units 11 and 12. A pair of the electrode protectors 30 are disposed for the discharging unit 11, and a pair of the electrode protectors 30 are disposed for the discharging unit 12.

When viewed in the direction of gas flow, the discharging unit 11 is interposed between the pair of electrode protectors 30. The discharging unit 11 is disposed between the pair of electrode protectors 30. When the discharge device 10 is viewed in the direction of gas flow, the discharging unit 11 can be seen between the pair of electrode protectors 30. Openings are formed upstream and downstream of the discharging unit 11 in the direction of gas flow, not to block the gas flow to the discharging unit 11. The pair of electrode protectors 30 for the discharging unit 12 are similarly formed.

The openings are disposed downstream of the discharging units 11 and 12. Thus, thin long adherents adhering to the discharging units 11 and 12 are prevented from allowing the discharging units 11 and 12 to come into contact with surrounding structures with the adherents and cause leakage. Thus, the discharge device 10 is prevented from degrading its discharging performance with time. The electrode protectors 30 are disposed without covering the discharging units 11 and 12. Thus, foreign matter adhering to the discharging units 11 and 12 can be easily removed with a cleaning device such as a cleaning brush or a cotton swab.

Each electrode protector 30 includes an upstream support 32, a downstream support 33, and a beam 37. The upstream support 32 and the downstream support 33 protrude perpendicularly to the surface of the housing 20. The direction in which the upstream support 32 and the downstream support 33 extend is parallel to the direction in which the discharging unit 11 extends. The upstream support 32 is disposed upstream of the discharging unit 11 in the direction of gas flow through the discharge device 10. The downstream support 33 is disposed downstream of the discharging unit 11 in the direction of gas flow. The upstream support 32 and the downstream support 33 are disposed without overlapping the discharging unit 11 in the direction of gas flow.

The beam 37 extends in the direction of gas flow. The tip end of the upstream support 32 is coupled to the upstream end of the beam 37 in the direction of gas flow. The tip end of the downstream support 33 is coupled to the downstream end of the beam 37 in the direction of gas flow. The tip ends of the upstream support 32 and the downstream support 33 protruding from the housing 20 are further apart from the housing 20 than the tip end of the discharging unit 11.

The upstream support 32 and the downstream support 33 are spaced apart from each other in the direction of gas flow. The electrode protector 30 has an arch shape. When the electrode protector 30 is viewed in the longitudinal direction of the housing 20, an opening having its three sides surrounded by the upstream support 32, the downstream support 33, and the beam 37 is formed, and the discharging unit 11 can be seen through this opening.

The upstream support 32 includes a root portion 34. The root portion 34 forms an end portion of the upstream support 32 closer to the housing 20. The root portion 34 is joined to the housing 20. The upstream support 32 is joined to the housing 20 at the root portion 34. The upstream support 32 is joined to the wall portion 21 of the housing 20. The downstream support 33 similarly includes a root portion 34.

Figure 4:
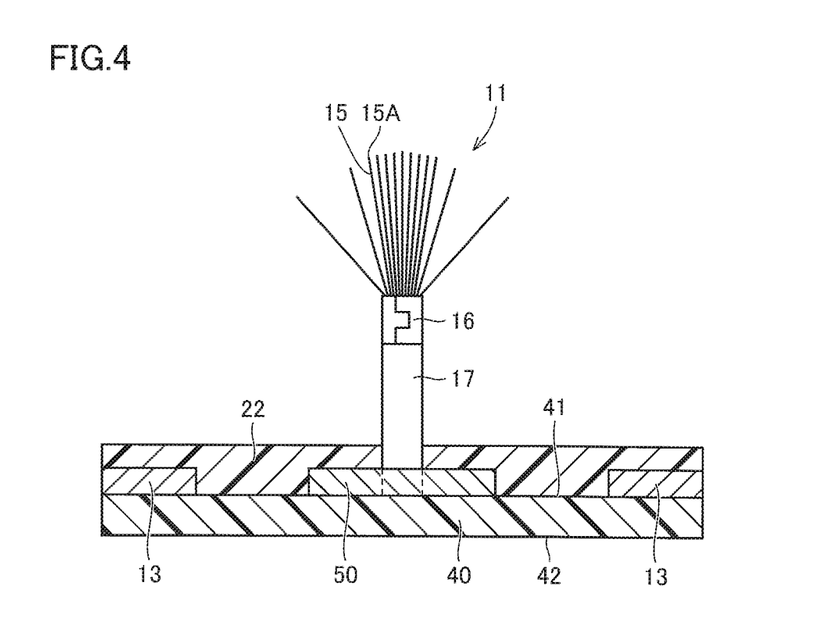
FIG. 4 is a cross-sectional view of the discharge device illustrated in FIG. 2, at a portion near a discharging unit.

FIG. 4 is a cross-sectional view of the discharge device 10 illustrated in FIG. 2, at a portion near the discharging unit 11. As illustrated in FIG. 4, inside the resin 22, induction electrodes (counter electrodes) 13, a substrate 40, and a second electrode 50 are embedded. The induction electrode 13, the substrate 40, and the second electrode 50 are disposed in the housing 20. The induction electrode 13, the substrate 40, and the second electrode 50 are insulated and sealed with the resin 22. The induction electrode 13, the substrate 40, and the second electrode 50 are entirely covered with the resin 22 without being exposed to the outside, and thus are not illustrated in FIGS. 2 and 3, which illustrate the external appearance of the discharge device 10.

The substrate 40 has a flat plate shape, and has a surface 41, which serves as a discharging surface, and a back surface 42, opposite to the surface 41. The substrate 40 supports the discharging unit 11. The discharging unit 11 is disposed perpendicularly to the surface 41 of the substrate 40, and fixed to the substrate 40. The discharging unit 11 protrudes from the surface 41 of the substrate 40. The discharging units 11 and 12 may be supported by the same substrate 40 or different substrates.

The substrate 40 supports the support portion 17 of the discharging unit 11. The support portion 17 is fixed to, for example, the substrate 40 with solder. The support portion 17 may be installed on the surface 41 of the substrate 40. The support portion 17 may extend through an opening formed in the substrate 40 and may be supported by the substrate 40 while extending through the substrate 40. Part of the support portion 17 may protrude from the back surface 42 of the substrate 40.

The induction electrode 13 is an electrode that forms an electric field between itself and the discharging unit 11. The induction electrode 13 is disposed around the discharging unit 11 and apart from the discharging unit 11. The induction electrode 13 is made of a conductive material such as metal.

The induction electrode 13 is disposed on the surface 41 of the substrate 40. The induction electrode 13 is formed of, for example, a conductor pattern formed on the surface 41 of the substrate 40. The induction electrode 13 may be formed of metal wires disposed apart from the surface 41 of the substrate 40. The induction electrode 13 may have an annular, typically, circular shape to surround the discharging unit 11, or another appropriate shape. The circular induction electrode 13 is disposed to have its center of the circle to almost coincide with the center of the electric conductors 15 bundled by the base portion 16.

The second electrode 50 receives a voltage having a polarity the same as that of the voltage applied to the discharging unit 11. The second electrode 50 is made of a conductive material such as metal. The second electrode 50 is disposed at the root portion of the discharging unit 11 that protrudes from the surface 41 of the substrate 40. The second electrode 50 is disposed on the surface 41 of the substrate 40. The second electrode 50 is in contact with the surface 41 of the substrate 40. The second electrode 50 may be formed of, for example, a conductor pattern disposed on the surface 41 of the substrate 40. Alternatively, the second electrode 50 may be formed of a member different from the substrate 40 installed on the surface 41.

The resin 22 laminated on the surface 41 of the substrate 40 has such a thickness as to tightly enclose the induction electrode 13 and the second electrode 50. The dimension of the second electrode 50 in the thickness direction of the substrate 40 is smaller than the thickness of the resin 22. On the other hand, the length by which the discharging unit 11 protrudes from the substrate 40 is larger than the thickness of the resin 22. The second electrode 50 is embedded in the resin 22, and the discharging unit 11 protrudes outward from the resin 22.

The second electrode 50 is disposed between the discharging unit 11 and the induction electrode 13. In the direction in which the surface 41 of the substrate 40 extends (direction such as the lateral direction in FIG. 4 or direction perpendicular to the plane of FIG. 4), the second electrode 50 is interposed between the discharging unit 11 and the induction electrode 13. When the discharge device 10 is viewed in the direction orthogonal to the surface 41 of the substrate 40 or in the direction in which the discharging unit 11 extends (vertical direction in FIG. 4), the second electrode 50 is disposed between the discharging unit 11 and the induction electrode 13.

The second electrode 50 is disposed closer to the discharging unit 11 than the induction electrode 13. The second electrode 50 is apart from a tip end 15A of the discharging unit 11 by a distance smaller than the shortest distance between the induction electrode 13 and the tip end 15A from which the discharging device 10 discharges in response to an application of a voltage. The shortest distance between the tip end 15A and the second electrode 50 is smaller than the shortest distance between the tip end 15A and the induction electrode 13.

The second electrode 50 has an annular, typically, circular shape to surround the discharging unit 11. The circular second electrode 50 is disposed to have its center of the circle to almost coincide with the center of the electric conductors 15 bundled by the base portion 16. The annular second electrode 50 has a diameter larger than the diameter of the discharging unit 11, typically, the diameter of the base portion 16 that bundles the electric conductors 15.

[Electric Circuit]

Figure 5:
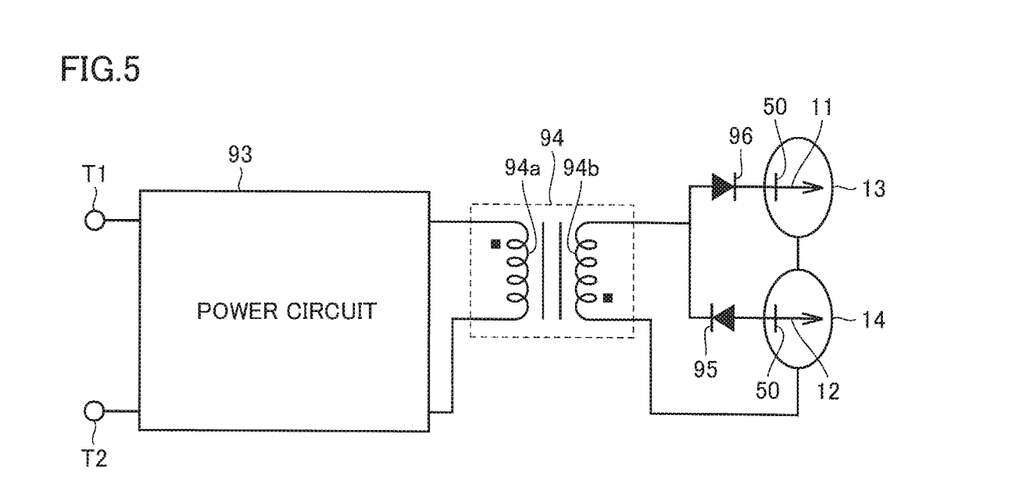
FIG. 5 is a circuit diagram of the structure of the discharge device illustrated in FIG. 2.

FIG. 5 is a circuit diagram of the structure of the discharge device 10 illustrated in FIG. 2. The discharge device 10 includes an induction electrode 14, which forms an electric field between itself and the discharging unit 12. The induction electrode 14 has the same structure as the induction electrode 13, which forms an electric field between itself and the discharging unit 11 and is illustrated with reference to FIG. 4. The discharge device 10 includes, in addition to the second electrode 50 corresponding to the discharging unit 11 described with reference to FIG. 4, a second electrode 50 corresponding to the discharging unit 12. The second electrode 50 corresponding to the discharging unit 12 has the same structure as the second electrode 50 corresponding to the discharging unit 11.

The discharge device 10 includes components such as a power supply terminal T1, a ground terminal T2, diodes 95 and 96, and a step-up transformer 94. The components in the circuit illustrated in FIG. 5 other than the discharging units 11 and 12, the induction electrode 13, and the second electrode 50 corresponding to the discharging unit 11 are not illustrated in other drawings.

A positive electrode and a negative electrode of the direct-current power supply are respectively connected to the power supply terminal T1 and the ground terminal T2. The power supply terminal T1 receives a direct-current power supply voltage (for example, +12 V or +15 V), and the ground terminal T2 is grounded. The power supply terminal T1 and the ground terminal T2 are connected to the step-up transformer 94 via a power circuit 93.

The step-up transformer 94 includes a primary coil 94a and a secondary coil 94b. The secondary coil 94b has its first terminal connected to the induction electrodes 13 and 14, and its second terminal connected to the anode of the diode 96 and the cathode of the diode 95. The cathode of the diode 96 is connected to the discharging unit 11 and the second electrode 50 corresponding to the discharging unit 11. The anode of the diode 95 is connected to the discharging unit 12 and the second electrode 50 corresponding to the discharging unit 12.

[Operation of Discharge Device 10]

The operation of the discharge device 10 will now be described. When a direct-current power supply voltage is applied across the power supply terminal T1 and the ground terminal T2, a capacitor (not illustrated) of the power circuit 93 is charged with electric charges. The electric charges with which the capacitor is charged are discharged via the primary coil 94a of the step-up transformer 94 to impress an impulse voltage on the primary coil 94a.

When an impulse voltage is impressed on the primary coil 94a, positive and negative high-voltage pulses are alternately impressed on the secondary coil 94b while attenuating. The positive high-voltage pulse is applied to the discharging unit 11 and the second electrode 50 via the diode 96, and the negative high-voltage pulse is applied to the discharging unit 12 and the second electrode 50 via the diode 95. Thus, the electric conductors 15 of the discharging units 11 and 12 cause corona discharge.

The discharging unit 11 may be, for example, a discharge electrode that generates positive ions. The discharging unit 12 may be, for example, a discharge electrode that generates negative ions. The discharging unit 11 generates positive ions by discharging in response to an application of a high voltage. The discharging unit 12 generates negative ions by discharging in response to an application of a high voltage.

The positive ions are cluster ions of multiple water molecules clustered around hydrogen ions ($H^+$), which are represented as $H^+(H_2O)_m$ (where m is any integer larger than or equal to 0). The negative ions are cluster ions of multiple water molecules clustered around oxygen ions ($O_2^-$), which are represented as $O_2^-(H_2O)_n$ (where n is any integer larger than or equal to 0). When the positive ions and negative ions are discharged into a room, both ions surround airborne mold or viruses, and cause chemical reaction with each other on their surfaces. With the effect of hydroxyl radicals (.OH), which are reactive species generated at this time, the airborne mold or another object are removed.

Operations and Effects

The characteristic structure, operations, and effects of the present embodiment will be collectively described as follows, although some part may be the same as the above description.

As illustrated in FIG. 5, the discharge device 10 according to the present embodiment includes the discharging unit 11 and the second electrode 50, which receives a voltage of the same polarity as that of the voltage applied to the discharging unit 11. As illustrated in FIG. 4, the second electrode 50 is disposed between the support portion 17 of the discharging unit 11 and the induction electrode 13.

As illustrated in FIG. 4, the second electrode 50 is disposed apart from the tip ends 15A of the electric conductors 15 by a distance smaller than the shortest distance between the induction electrode 13 and the tip end 15A.

Compared to an existing structure that does not include a second electrode, in the structure including the second electrode 50 disposed closer to the discharging unit 11 than the induction electrode 13, the shape of a line of electric force directing from the tip ends 15A of the electric conductors 15 toward the induction electrode 13 changes.

Specifically, a line of electric force directing from the tip ends 15A of the electric conductors 15 toward the induction electrode 13 takes a detour around the second electrode 50. The line of electric force directing from the tip ends 15A of the electric conductors 15 toward the induction electrode 13 extends to avoid the second electrode 50. The line of electric force directing from the tip ends 15A of the electric conductors 15 toward the induction electrode 13 is not drawn near the second electrode 50. The line of electric force directing from the tip ends 15A of the electric conductors 15 toward the induction electrode 13 is drawn at a position further from the discharging unit 11 than in an existing structure.

Reactive species that occur as a result of a discharge of the discharging unit 11 move away from the tip ends 15A along the line of electric force. With the flow of gas around the discharging unit 11, the reactive species move away from the line of electric force, and are transported by the flow of gas. In the present embodiment, the line of electric force along which the reactive species move has a shape that takes a detour around the second electrode 50. Thus, the reactive species are dispersed over a wider range, and are more easily transported by gas. This structure can thus prevent the reactive species from being collected by the substrate 40, the resin 22, or the induction electrode 13. The discharge device 10 according to the present embodiment can thus discharge a larger amount of reactive species to the outside, and improve the efficiency of generating reactive species such as ions.

Instead of the structure where the discharge device 10 includes the second electrode 50, the line of electric force directing from the tip ends 15A of the electric conductors 15 to the induction electrode 13 can be also changed by increasing the distance between the discharging unit 11 and an induction electrode 13 having a larger diameter. In this case, however, the outside dimensions of the discharge device 10 increase to secure the distance between the discharging unit 11 and the induction electrode 13. As in the case of the discharge device 10 according to the present embodiment, the structure including the second electrode 50 without changing the shape of the induction electrode 13 can improve the efficiency of generating reactive species without the need of increasing the size of the discharge device 10.

As illustrated in FIG. 4, the discharging unit 11 is a brush-shaped electrode including multiple linear electric conductors 15 and a base portion 16 that bundles the electric conductors 15. The electric conductors 15 have a thread shape with a small diameter and are bendable. When a high voltage is applied to the discharging unit 11, the electric conductors 15 having the same polarity electrically repel each other and form a shape of an open brush end.

While the discharge device 10 is used for a long time, one or more electric conductors 15 may be electrically attracted to the induction electrode 13 having a different polarity and may bend to a large extent. Even in this case, the electric conductors 15 repel the second electrode 50 having the same polarity as that of the electric conductors 15, so that the electric conductors 15 are prevented from bending substantially 180° toward the surface 41 of the substrate 40. Even when the electric conductors 15 bend, the tip ends 15A of the electric conductors 15 are prevented from directly touching the substrate 40, the resin 22, or the induction electrode 13. This structure reliably prevents the electric conductors 15 from abnormally discharging at a contact portion at which they come into contact with a member having a different polarity to reduce the amount of reactive species generated. Thus, the discharge device 10 according to the present embodiment can retain the amount of reactive species generated after an elapse of time and keep the discharging performance for a long time.

By optimizing the shape of the second electrode 50, the shape into which the brush formed of the electric conductors 15 opens can be adjusted to be appropriate for improving the efficiency of generating reactive species. Thus, the discharge device 10 that can further improve the efficiency of generating reactive species can be achieved.

As illustrated in FIG. 4, the discharge device 10 further includes the resin 22 with which the induction electrode 13 and the second electrode 50 are sealed. In this structure, only the discharging unit 11 that discharges in response to an application of a voltage protrudes from the resin 22, so that the induction electrode 13 or the second electrode 50 can be prevented from corroding with the effect of the environment. This structure can thus prevent an occurrence of leakage at the induction electrode 13 or the second electrode 50, and can keep the performance of the discharge device 10 for a long time.

As illustrated in FIG. 4, the second electrode 50 is disposed at the root portion of the discharging unit 11 that protrudes from the surface 41 of the substrate 40. Here, a structure formed from the discharging unit 11 and the second electrode 50 can have a shape stable with respect to the substrate 40, and thus can improve the strength of the support portion 17.

As illustrated in FIG. 4, the second electrode 50 is disposed on the surface 41 of the substrate 40. Thus, the second electrode 50 can be formed of a conductor pattern on the surface 41 of the substrate 40, so that the second electrode 50 can be easily formed at low costs. As illustrated in FIG. 4, in the structure where the induction electrode 13 and the second electrode 50 are both disposed on the surface 41 of the substrate 40, the second electrode 50 can be reliably disposed between the discharging unit 11 and the induction electrode 13.

Second Embodiment

Figure 6:
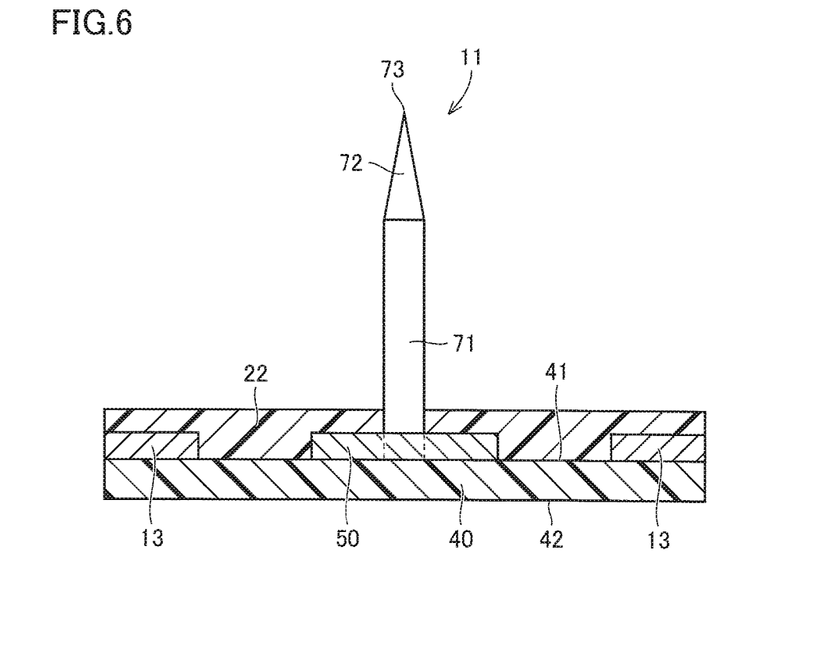
FIG. 6 is a cross-sectional view of a discharge device according to a second embodiment, at a portion near the discharging unit.

FIG. 6 is a cross-sectional view of the discharge device 10 according to a second embodiment, at a portion near the discharging unit 11. In the first embodiment, the discharging units 11 and 12 have a brush-shaped structure including the linear electric conductors 15. In the second embodiment, on the other hand, needle electrodes constitute the discharging units 11 and 12. The discharging unit 11 according to the second embodiment includes a columnar portion 71, a conical portion 72, and a pointed end 73. The columnar portion 71 is fixed to the substrate 40. In response to an application of a high voltage to the discharging unit 11, the discharging unit 11 discharges at the pointed end 73 to generate ions. The pointed end 73 functions as a tip portion of the discharging unit 11 according to the second embodiment.

Also in the second embodiment, the second electrode 50 is disposed at the root portion of the discharging unit 11 that protrudes from the surface 41 of the substrate 40. Since the second electrode 50 is disposed between the discharging unit 11 and the induction electrode 13, also when the discharging unit 11 is formed of a needle electrode, a line of electric force directing from the pointed end 73 to the induction electrode 13 takes a detour around the second electrode 50. Thus, reactive species generated at the pointed end 73 are easily transported by gas, and prevented from being collected by the substrate 40, the resin 22, or the induction electrode 13. This structure can thus achieve an effect of improving the efficiency of generating reactive species, as in the case of the first embodiment.

The discharging units 11 and 12 may include an electrode of a stick, linear, fiber, or sheet shape instead of a brush or needle shape.

Third Embodiment

Figure 7:
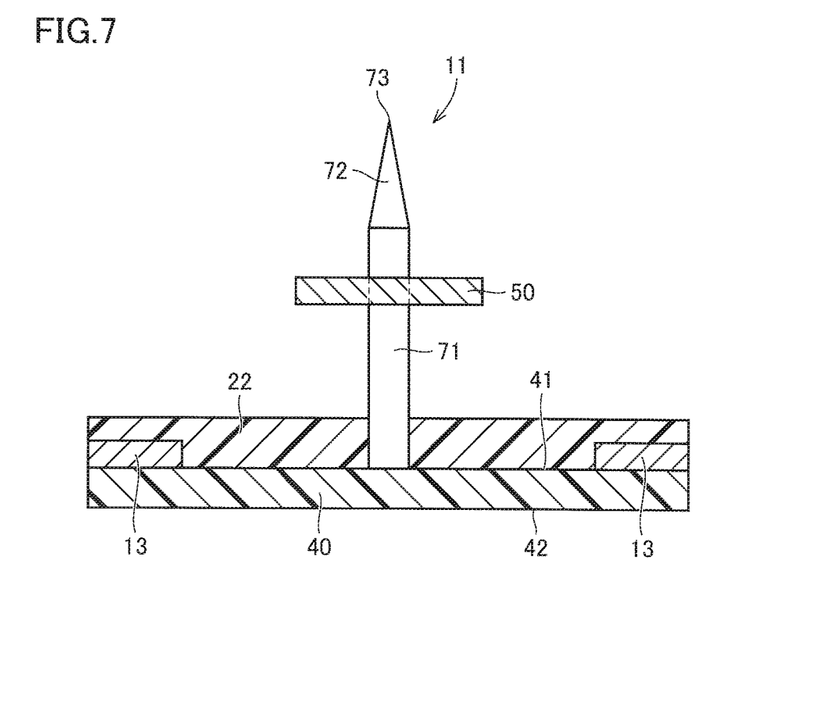
FIG. 7 is a cross-sectional view of a discharge device according to a third embodiment, at a portion near the discharging unit.

FIG. 7 is a cross-sectional view of a discharge device 10 according to a third embodiment, at a portion near the discharging unit 11. In the third embodiment, the second electrode 50 is disposed, instead of at the root portion of the discharging unit 11, at a middle portion of the discharging unit 11 in a protrusion direction in which the discharging unit 11 protrudes from the surface 41 of the substrate 40. The root portion of the discharging unit 11 is sealed with the resin 22, whereas the second electrode 50 is not sealed with the resin 22. The second electrode 50 is exposed to the outside without being embedded in the resin 22.

Also in the arrangement illustrated in FIG. 7, the second electrode 50 is disposed between the discharging unit 11 and the induction electrode 13. In the direction in which the surface 41 of the substrate 40 extends (direction such as the lateral direction in FIG. 7 or the direction perpendicular to the plane of FIG. 7), the second electrode 50 is interposed between the discharging unit 11 and the induction electrode 13. When the discharge device 10 is viewed in the direction perpendicular to the surface 41 of the substrate 40 or the direction in which the discharging unit 11 extends (vertical direction in FIG. 7), the second electrode 50 is disposed between the discharging unit 11 and the induction electrode 13.

Since the second electrode 50 is disposed between the discharging unit 11 and the induction electrode 13, the line of electric force directing from the pointed end 73 to the induction electrode 13 takes a detour around the second electrode 50. Thus, reactive species generated at the pointed end 73 are easily transported by gas, and prevented from being collected by the substrate 40, the resin 22, or the induction electrode 13. This structure can thus have an effect of improving the efficiency of generating reactive species, as in the case of the first embodiment.

The second electrode 50 may be formed by fixing a circular member different from the needle-shaped discharging unit 11 to the columnar portion 71 of the discharging unit 11. Alternatively, the second electrode 50 may be formed integrally with the needle-shaped discharging unit 11 by deforming a middle portion of the discharging unit 11 to have a larger diameter. For example, the second electrode 50 may be formed by deforming the discharging unit 11 with a pressure applied thereto in the longitudinal direction of the needle-shaped discharging unit 11.

Also in the case of the discharging unit 11 having a brush shape described in the first embodiment, the second electrode 50 may be formed integrally with the support portion 17 or the base portion 16.

Fourth Embodiment

Figure 8:
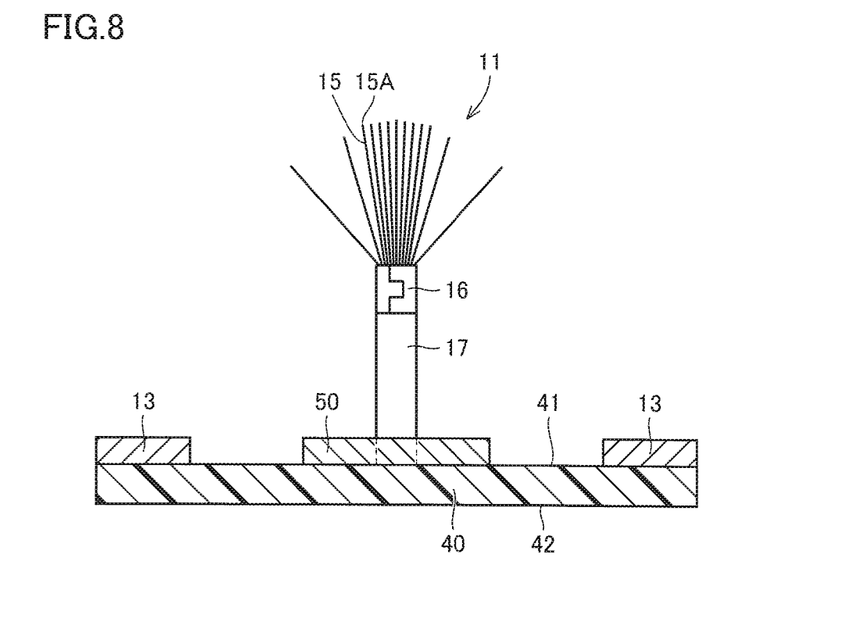
FIG. 8 is a cross-sectional view of a discharge device according to a fourth embodiment, at a portion near the discharging unit.

FIG. 8 is a cross-sectional view of a discharge device 10 according to a fourth embodiment, at a portion near the discharging unit 11. As in the case of the first embodiment, in the discharge device 10 according to the fourth embodiment, the induction electrode 13 and the second electrode 50 are disposed on the surface 41 of the substrate 40. The discharge device 10 according to the fourth embodiment is different from that according to the first embodiment in that a resin layer is not laminated on the surface 41 of the substrate 40, so that the induction electrode 13 and the second electrode 50 are not sealed with resin.

When the discharge device 10 is used under the environment where the electrode does not corrode during a long use of the discharge device 10, as illustrated in FIG. 8, the induction electrode 13 and the second electrode 50 may be left exposed without being covered with resin. Keeping the second electrode 50 exposed without being covered with resin can further increase the effect of the line of electric force directing from the tip ends 15A of the electric conductors 15 to the induction electrode 13 on the second electrode 50. This structure can thus more significantly obtain the effect of changing the shape of the line of electric force directing from the tip ends 15A of the electric conductors 15 to the induction electrode 13 into a shape that takes a detour around the second electrode 50.

As described in the first to third embodiments, in the structure where the second electrode 50 is covered with resin with a thickness not too large, the above-described effect of forming a line of electric force that takes a detour around the second electrode 50 is obtained by charging the resin that covers the second electrode 50. Preferably, the thickness of a resin layer laminated on the surface 41 of the substrate 40 is smallest possible to seal the induction electrode 13 and second electrode 50. For example, the resin layer may have a thickness of smaller than or equal to 2 mm.

Fifth Embodiment

Figure 9:
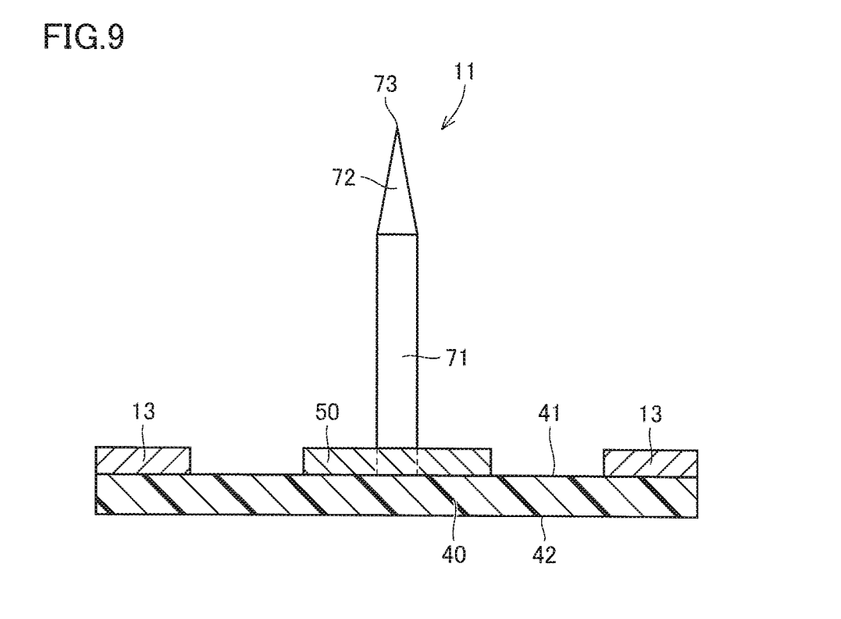
FIG. 9 is a cross-sectional view of a discharge device according to a fifth embodiment, at a portion near the discharging unit.

FIG. 9 is a cross-sectional view of a discharge device 10 according to a fifth embodiment, at a portion near the discharging unit 11. The discharge device 10 according to the fifth embodiment is different from that according to the third embodiment in that a resin layer is not laminated on the surface 41 of the substrate 40 and the induction electrode 13 and the second electrode 50 are not sealed with resin. This structure can thus more significantly obtain the effect of changing the shape of the line of electric force directing from the pointed end 73 to the induction electrode 13 into a shape that takes a detour around the second electrode 50, as in the case of the fourth embodiment.

Sixth Embodiment

Figure 10:
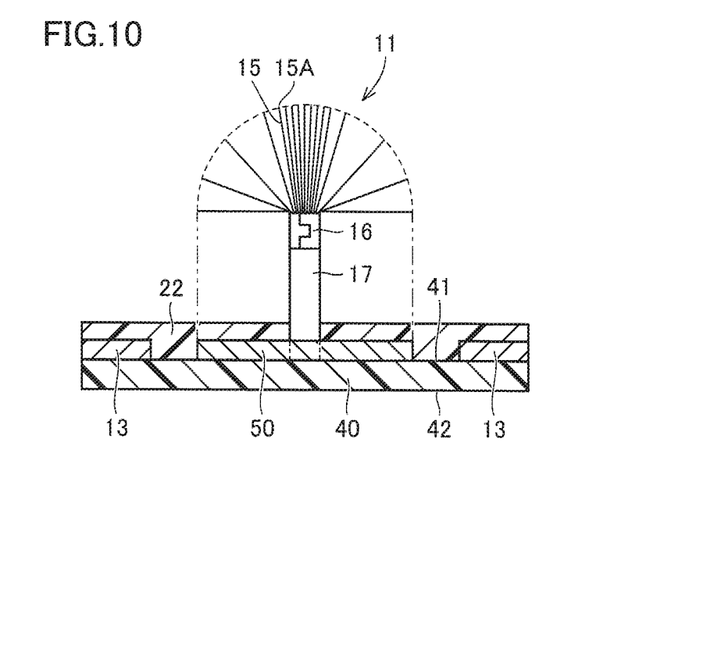
FIG. 10 is a cross-sectional view of a discharge device according to a sixth embodiment, at a portion near the discharging unit.
Figure 11:
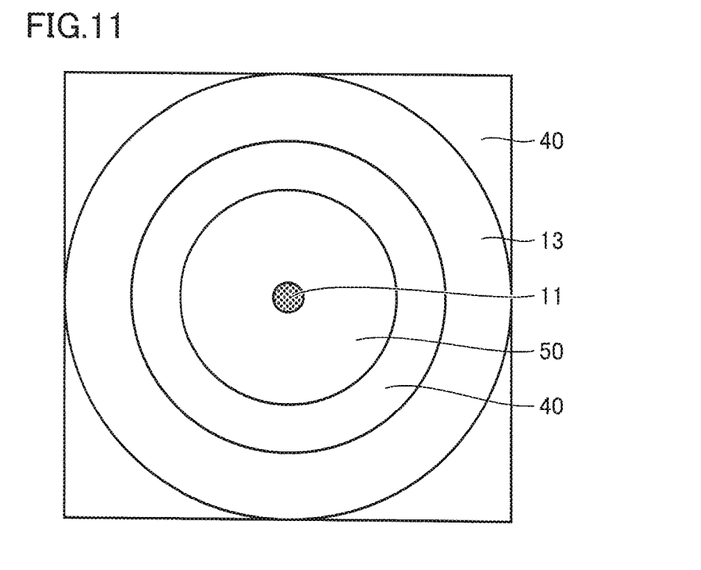
FIG. 11 is a plan view of the discharge device according to the sixth embodiment, at a portion near the discharging unit.

FIG. 10 is a cross-sectional view of a discharge device 10 according to a sixth embodiment, at a portion near the discharging unit 11. FIG. 11 is a plan view of the discharge device 10 according to the sixth embodiment, at a portion near the discharging unit 11. FIG. 11 does not illustrate the resin 22. In response to an application of a high voltage to the discharging unit 11, multiple linear electric conductors 15 illustrated in FIG. 10 form a shape of an open brush end.

A broken line in FIG. 10 denotes a locus of the tip ends 15A of the electric conductors 15 that move in response to an application of a high voltage. The substantially arc-shaped area inside the broken line represents a movable range within which the multiple linear electric conductors 15 are movable. Two-dot chain lines in FIG. 10 represent projection lines of the movable range of the electric conductor 15 projected on the surface 41 of the substrate 40. As illustrated in FIGS. 10 and 11, the second electrode 50 has a shape substantially the same as an image of the movable range of the electric conductors 15 projected on the surface 41 of the substrate 40. The second electrode 50 has a disc shape having a diameter substantially the same as that of the projection of the movable range of the electric conductors 15 on the surface 41.

Discharge occurs at the tip ends 15A of the electric conductors 15. If the second electrode 50 is smaller than the movable range of the electric conductors 15, the effect with which the second electrode 50 changes the shape of the line of electric force directing from the tip ends 15A of the electric conductors 15 to the induction electrode 13 is reduced. If the second electrode 50 is larger than the movable range of the electric conductors 15, the distance between the discharging unit 11 and the induction electrode 13 increases, which adversely affects discharge stability and size reduction of the discharge device 10. The second electrode 50 having a disk shape with a diameter substantially the same as that of the projection of the movable range of the electric conductors 15 on the surface 41 can disperse reactive species to a wider area.

Seventh Embodiment

Figure 12:
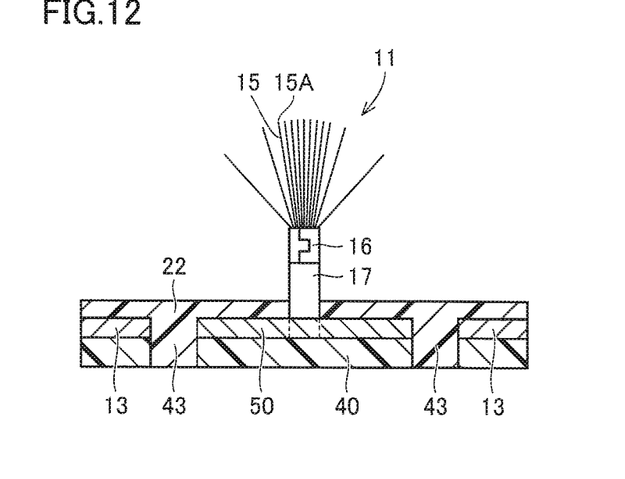
FIG. 12 is a cross-sectional view of a discharge device according to a seventh embodiment, at a portion near the discharging unit.
Figure 13:
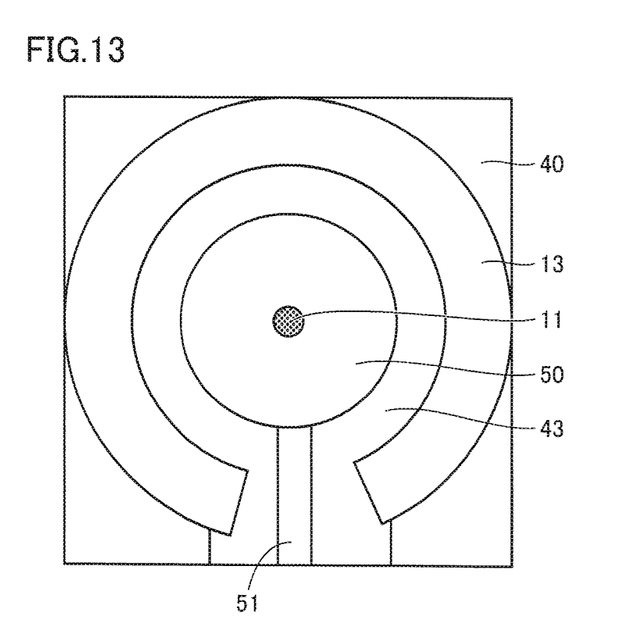
FIG. 13 is a plan view of the discharge device according to the seventh embodiment, at a portion near the discharging unit.

FIG. 12 is a cross-sectional view of a discharge device 10 according to a seventh embodiment, at a portion near the discharging unit 11. FIG. 13 is a plan view of the discharge device 10 according to the seventh embodiment, at a portion near the discharging unit 11. FIG. 13 does not illustrate the resin 22. In the discharge device 10 according to the seventh embodiment, the second electrode 50 and the induction electrode 13 are both disposed on the surface 41 of the substrate 40. A slit 43, at which the surface 41 of the substrate 40 is recessed, is disposed between the second electrode 50 and the induction electrode 13. The slit 43 is filled with the resin 22. A power feed portion 51, which is electrically connected to the second electrode 50, is disposed on the substrate 40. Power is fed to the second electrode 50 via the power feed portion 51.

In a structure where the second electrode 50 and the induction electrode 13 are disposed on the surface 41 of the substrate 40 and the surface 41 of the substrate 40 between the second electrode 50 and the induction electrode 13 has a flat shape, the distance between the discharging unit 11 and the induction electrode 13 needs to be increased to secure an insulation distance between the discharging unit 11 and the induction electrode 13. Here, the outside dimensions of the discharge device 10 increase to secure the distance between the discharging unit 11 and the induction electrode 13, so that size reduction of the discharge device 10 fails. As illustrated in FIGS. 12 and 13, a creepage distance for insulation between the discharging unit 11 and the induction electrode 13 can be increased by forming the slit 43 between the second electrode 50 and the induction electrode 13. This structure can secure insulation between the discharging unit 11 and the induction electrode 13 without the need of disposing the discharging unit 11 and the induction electrode 13 apart from each other.

Sealing the slit 43 with the resin 22 as illustrated in FIG. 12 can more reliably secure insulation between the discharging unit 11 and the induction electrode 13.

The embodiments have been described thus far. The embodiments may be combined as appropriate. The embodiments disclosed herein should be understood as being mere examples and not limitative in all respect. The scope of the present invention is defined by the scope of claims, instead of the above description, and is intended to include the equivalents to the scope of claims, and all changes within the scope.

REFERENCE SIGNS LIST 1 outer casing
2 duct
3 first outlet
4 second outlet
5 blower
6 inlet port
7 grille
8 filter
9 fan guard
10 discharge device
11, 12 discharging unit
13, 14 induction electrode
15 electric conductor
15A tip end 16 base portion
17 support portion
20 housing
21 wall portion
22 resin
23 connector
30 electrode protector
32 upstream support
33 downstream support
34 root portion
37 beam
40 substrate
41 surface
42 back surface
43 slit
50 second electrode
51 power feed portion
71 columnar portion
72 conical portion
73 pointed end
93 power circuit
100 air cleaner

The invention claimed is:

1. A discharge device, comprising:
a discharging unit that includes a tip end and discharges from the tip end in response to an application of a voltage;
an induction electrode that forms an electric field between the induction electrode and the discharging unit; and
a second electrode that is disposed between the discharging unit and the induction electrode, the second electrode being made of a conductive material and receiving a voltage having a polarity the same as a polarity of the voltage applied to the discharging unit.

2. The discharge device according to claim 1, wherein the second electrode is spaced apart from the tip end by a distance smaller than a shortest distance between the tip end and the induction electrode.

3. The discharge device according to claim 1, further comprising resin with which the induction electrode and the second electrode are sealed.

4. The discharge device according to claim 1, further comprising a substrate that includes a surface and supports the discharging unit,
wherein the second electrode is disposed at a root portion of the discharging unit that protrudes from the surface of the substrate.

5. The discharge device according to claim 4, wherein the second electrode is disposed on the surface of the substrate.

6. The discharge device according to claim 5,
wherein the induction electrode is disposed on the surface of the substrate, and
wherein the surface of the substrate has a slit recessed between the second electrode and the induction electrode.

7. The discharge device according to claim 1, wherein the discharging unit includes a plurality of linear electric conductors and a base portion that bundles the electric conductors.

8. The discharge device according to claim 7, further comprising a substrate that includes a surface and supports the discharging unit,
wherein the second electrode has a disk shape having a substantially the same diameter as a diameter of a projection of a movable range of the electric conductors on the surface.

9. An electric machine, comprising:
the discharge device according to claim 1; and
a blower that feeds gas to the discharge device.

* * * * *